(12) United States Patent
Morita

(10) Patent No.: US 10,159,404 B2
(45) Date of Patent: Dec. 25, 2018

(54) ENDOSCOPE APPARATUS

(71) Applicant: OLYMPUS CORPORATION, Tokyo (JP)

(72) Inventor: Yasunori Morita, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 443 days.

(21) Appl. No.: 15/168,301

(22) Filed: May 31, 2016

(65) Prior Publication Data

US 2016/0270642 A1 Sep. 22, 2016

Related U.S. Application Data

(63) Continuation of application No. PCT/JP2014/082026, filed on Dec. 3, 2014.

(30) Foreign Application Priority Data

Dec. 20, 2013 (JP) .................................. 2013-264062

(51) Int. Cl.
*A61B 1/04* (2006.01)
*A61B 1/06* (2006.01)
(Continued)

(52) U.S. Cl.
CPC ........ *A61B 1/0646* (2013.01); *A61B 1/00009* (2013.01); *A61B 1/00045* (2013.01);
(Continued)

(58) Field of Classification Search
CPC .............. A61B 1/0646; A61B 1/00045; A61B 1/00112; A61B 1/0052; A61B 1/06; A61B 1/0638; A61B 1/0676
(Continued)

(56) References Cited

U.S. PATENT DOCUMENTS 4,885,634 A * 12/1989 Yabe .................. A61B 1/00039
348/71
5,852,468 A * 12/1998 Okada .................... H04N 9/045
348/272

(Continued)

FOREIGN PATENT DOCUMENTS

EP 1 862 967 A1 12/2007
EP 2 328 339 A2 6/2011
(Continued)

OTHER PUBLICATIONS

Chinese Office Action dated Dec. 19, 2017 in Chinese Patent Application No. 201480068983.0.
(Continued)

*Primary Examiner* — Timothy J Neal
*Assistant Examiner* — Jae Woo
(74) *Attorney, Agent, or Firm* — Scully, Scott, Murphy & Presser, P.C.

(57) ABSTRACT

An endoscope apparatus includes: a light source that emits white light or narrow-band light; an image sensor having pixels; a color filter including a filter unit having a plurality of filters in which the number of filters for passing green wavelength band light and the number of filters for passing blue wavelength band light satisfy predetermined conditions; a first gain adjustment unit that adjusts a gain of an electric signal generated by the image sensor; a demosaicing processing unit that generates an image signal of a color component passing through a filter based on the electric signal whose gain has been adjusted by the first gain adjustment unit; a color conversion processing unit that performs color separation on an image signal when the light source unit emits the white light; and a second gain adjustment unit that adjusts a gain of each image signal subjected to the color conversion processing.

5 Claims, 9 Drawing Sheets

(51) Int. Cl.
*H04N 5/225* (2006.01)
*A61B 1/00* (2006.01)
*A61B 1/005* (2006.01)
*A61B 1/018* (2006.01)
*A61B 1/05* (2006.01)
*H04N 9/083* (2006.01)
*G02B 23/24* (2006.01)
*H04N 7/18* (2006.01)

(52) U.S. Cl.
CPC ........ *A61B 1/0052* (2013.01); *A61B 1/00112* (2013.01); *A61B 1/018* (2013.01); *A61B 1/04* (2013.01); *A61B 1/05* (2013.01); *A61B 1/06* (2013.01); *A61B 1/0638* (2013.01); *A61B 1/0676* (2013.01); *H04N 5/2256* (2013.01); *H04N 9/083* (2013.01); *G02B 23/2469* (2013.01); *H04N 7/18* (2013.01); *H04N 2005/2255* (2013.01)

(58) Field of Classification Search
USPC .......................................................... 600/109
See application file for complete search history.

(56) References Cited

U.S. PATENT DOCUMENTS

| | | | | |
|---|---|---|---|---|
| 9,282,302 | B2* | 3/2016 | Uchihara | H04N 9/646 |
| 2005/0154262 | A1* | 7/2005 | Banik | A61B 1/00059 |
| | | | | 600/179 |
| 2005/0197536 | A1* | 9/2005 | Banik | A61B 1/00059 |
| | | | | 600/179 |
| 2009/0021578 | A1* | 1/2009 | Yamazaki | A61B 1/0638 |
| | | | | 348/65 |
| 2011/0112362 | A1* | 5/2011 | Minetoma | A61B 1/05 |
| | | | | 600/109 |
| 2012/0105612 | A1* | 5/2012 | Yoshino | A61B 1/00009 |
| | | | | 348/65 |
| 2012/0147165 | A1* | 6/2012 | Yoshino | H04N 5/23212 |
| | | | | 348/65 |
| 2012/0197077 | A1* | 8/2012 | Kaku | A61B 1/00009 |
| | | | | 600/109 |
| 2013/0152020 | A1* | 6/2013 | Nishiyama | A61B 1/00009 |
| | | | | 715/835 |
| 2016/0270642 | A1* | 9/2016 | Morita | A61B 1/04 |
| 2017/0014055 | A1* | 1/2017 | Otani | A61B 5/1459 |
| 2017/0018083 | A1* | 1/2017 | Kuramoto | A61B 5/1032 |
| 2017/0231469 | A1* | 8/2017 | Kaku | A61B 1/00006 |
| | | | | 600/479 |
| 2017/0251932 | A1* | 9/2017 | Kaku | A61B 1/00009 |
| 2017/0319051 | A1* | 11/2017 | Kuriyama | A61B 1/00006 |
| 2017/0360287 | A1* | 12/2017 | Morimoto | A61B 1/0638 |
| 2018/0007256 | A1* | 1/2018 | Yoshino | G02B 23/24 |
| 2018/0020903 | A1* | 1/2018 | Saito | A61B 1/04 |
| | | | | 382/128 |
| 2018/0033142 | A1* | 2/2018 | Morita | A61B 1/04 |
| 2018/0042468 | A1* | 2/2018 | Teramura | G06T 7/0012 |
| 2018/0049679 | A1* | 2/2018 | Chiba | A61B 1/00009 |
| 2018/0214005 | A1* | 8/2018 | Ebata | A61B 1/04 |
| 2018/0218499 | A1* | 8/2018 | Kamon | A61B 1/00 |
| 2018/0242893 | A1* | 8/2018 | Saito | A61B 1/00 |
| 2018/0249889 | A1* | 9/2018 | Imai | A61B 1/00009 |

FOREIGN PATENT DOCUMENTS

| | | |
|---|---|---|
| EP | 2 334 084 A1 | 6/2011 |
| EP | 2 481 342 A1 | 8/2012 |
| JP | S60-089187 A | 5/1985 |
| JP | H08-237672 A | 9/1996 |
| JP | 2013-208284 A | 10/2013 |
| JP | 2014-103597 A | 6/2014 |

OTHER PUBLICATIONS

Extended Supplementary European Search Report dated Jul. 25, 2017 in European Patent Application No. 14 87 1730.9.
International Search Report dated Mar. 10, 2015 issued in PCT/JP2014/082026.

* cited by examiner

FIG.3

| $P_{11}$ | $P_{12}$ | $P_{13}$ | $P_{14}$ | ⋯ |
|---|---|---|---|---|
| $P_{21}$ | $P_{22}$ | $P_{23}$ | $P_{24}$ | ⋯ |
| $P_{31}$ | $P_{32}$ | $P_{33}$ | $P_{34}$ | ⋯ |
| $P_{41}$ | $P_{42}$ | $P_{43}$ | $P_{44}$ | ⋯ |
| ⋮ | ⋮ | ⋮ | ⋮ | ⋱ |

| $B_{11}$ | $G_{12}$ | $B_{13}$ | $G_{14}$ | ⋯ |
|---|---|---|---|---|
| $G_{21}$ | $Mg_{22}$ | $G_{23}$ | $Mg_{24}$ | ⋯ |
| $B_{31}$ | $G_{32}$ | $B_{33}$ | $G_{34}$ | ⋯ |
| $G_{41}$ | $Mg_{42}$ | $G_{43}$ | $Mg_{44}$ | ⋯ |
| ⋮ | ⋮ | ⋮ | ⋮ | ⋱ |

FIG.9

| | U3 | | |
|---|---|---|---|
| $B_{11}$ | $Cy_{12}$ | $B_{13}$ | $Cy_{14}$ | $\cdots$ |
| $Cy_{21}$ | $Mg_{22}$ | $Cy_{23}$ | $Mg_{24}$ | $\cdots$ |
| $B_{31}$ | $Cy_{32}$ | $B_{33}$ | $Cy_{34}$ | $\cdots$ |
| $Cy_{41}$ | $Mg_{42}$ | $Cy_{43}$ | $Mg_{44}$ | $\cdots$ |
| $\vdots$ | $\vdots$ | $\vdots$ | $\vdots$ | $\ddots$ |

FIG.10

| | U4 | | |
|---|---|---|---|
| $B_{11}$ | $Cy_{12}$ | $B_{13}$ | $Cy_{14}$ | $\cdots$ |
| $Cy_{21}$ | $W_{22}$ | $Cy_{23}$ | $W_{24}$ | $\cdots$ |
| $B_{31}$ | $Cy_{32}$ | $B_{33}$ | $Cy_{34}$ | $\cdots$ |
| $Cy_{41}$ | $W_{42}$ | $Cy_{43}$ | $W_{44}$ | $\cdots$ |
| $\vdots$ | $\vdots$ | $\vdots$ | $\vdots$ | $\ddots$ |

FIG.11

| U5 | | | | | | | | |
|---|---|---|---|---|---|---|---|---|
| $B_{11}$ | $G_{12}$ | $Mg_{13}$ | $G_{14}$ | $B_{15}$ | $G_{16}$ | $Mg_{17}$ | $G_{18}$ | ⋯ |
| $G_{21}$ | $Mg_{22}$ | $G_{23}$ | $B_{24}$ | $G_{25}$ | $Mg_{26}$ | $G_{27}$ | $B_{28}$ | ⋯ |
| $Mg_{31}$ | $G_{32}$ | $B_{33}$ | $G_{34}$ | $Mg_{35}$ | $G_{36}$ | $B_{37}$ | $G_{38}$ | ⋯ |
| $G_{41}$ | $B_{42}$ | $G_{43}$ | $Mg_{44}$ | $G_{45}$ | $B_{46}$ | $G_{47}$ | $Mg_{48}$ | ⋯ |
| $B_{51}$ | $G_{52}$ | $Mg_{53}$ | $G_{54}$ | $B_{55}$ | $G_{56}$ | $Mg_{57}$ | $G_{58}$ | ⋯ |
| $G_{61}$ | $Mg_{62}$ | $G_{63}$ | $B_{64}$ | $G_{65}$ | $Mg_{66}$ | $G_{67}$ | $B_{68}$ | ⋯ |
| $Mg_{71}$ | $G_{72}$ | $B_{73}$ | $G_{74}$ | $Mg_{75}$ | $G_{76}$ | $B_{77}$ | $G_{78}$ | ⋯ |
| $G_{81}$ | $B_{82}$ | $G_{83}$ | $Mg_{84}$ | $G_{85}$ | $B_{86}$ | $G_{87}$ | $Mg_{88}$ | ⋯ |
| ⋮ | ⋮ | ⋮ | ⋮ | ⋮ | ⋮ | ⋮ | ⋮ | ⋱ |

FIG.12

| | | | | | | | | |
|---|---|---|---|---|---|---|---|---|
| $B_{11}$ | $W_{12}$ | $Mg_{13}$ | $W_{14}$ | $B_{15}$ | $W_{16}$ | $Mg_{17}$ | $W_{18}$ | ⋯ |
| $W_{21}$ | $Mg_{22}$ | $W_{23}$ | $B_{24}$ | $W_{25}$ | $Mg_{26}$ | $W_{27}$ | $B_{28}$ | ⋯ |
| $Mg_{31}$ | $W_{32}$ | $B_{33}$ | $W_{34}$ | $Mg_{35}$ | $W_{36}$ | $B_{37}$ | $W_{38}$ | ⋯ |
| $W_{41}$ | $B_{42}$ | $W_{43}$ | $Mg_{44}$ | $W_{45}$ | $B_{46}$ | $W_{47}$ | $Mg_{48}$ | ⋯ |
| $B_{51}$ | $W_{52}$ | $Mg_{53}$ | $W_{54}$ | $B_{55}$ | $W_{56}$ | $Mg_{57}$ | $W_{58}$ | ⋯ |
| $W_{61}$ | $Mg_{62}$ | $W_{63}$ | $B_{64}$ | $W_{65}$ | $Mg_{66}$ | $W_{67}$ | $B_{68}$ | ⋯ |
| $Mg_{71}$ | $W_{72}$ | $B_{73}$ | $W_{74}$ | $Mg_{75}$ | $W_{76}$ | $B_{77}$ | $W_{78}$ | ⋯ |
| $W_{81}$ | $B_{82}$ | $W_{83}$ | $Mg_{84}$ | $W_{85}$ | $B_{86}$ | $W_{87}$ | $Mg_{88}$ | ⋯ |
| ⋮ | ⋮ | ⋮ | ⋮ | ⋮ | ⋮ | ⋮ | ⋮ | ⋱ |

U6

ENDOSCOPE APPARATUS

CROSS REFERENCES TO RELATED APPLICATIONS

This application is a continuation of PCT international application Ser. No. PCT/JP2014/082026, filed on Dec. 3, 2014 which designates the United States, incorporated herein by reference, and which claims the benefit of priority from Japanese Patent Application No. 2013-264062, filed on Dec. 20, 2013, incorporated herein by reference.

BACKGROUND

1. Technical Field

The disclosure relates to an endoscope apparatus configured to be introduced into a living body to capture images inside the living body.

2. Related Art

In the related art, an endoscope apparatus is widely used for various kinds of examinations in a medical field and an industrial field. Among such endoscope apparatus, a medical endoscope apparatus is capable of capturing an in-vivo image inside a body cavity even without cutting a subject by introducing, into the body cavity of the subject such as a patient, an insertion portion provided with an image sensor including a plurality of pixels, formed in a thin long shape, and having flexibility. Therefore, there is little burden on the subject and the medical endoscope apparatus is more widely used.

As an observation method of such an endoscope apparatus, a white light imaging (WLI) method using white illumination light; and a narrow band imaging (NBI) method using illumination light formed of two kinds of narrow-band light respectively included in blue and green wavelength bands (narrow-band illumination light) are already known. Among these, the narrow band imaging method is capable of obtaining an image in which capillary vessels, microscopic patterns of a mucosa, and the like existing in a mucous membrane surface layer of the living body can be displayed in a highlighted manner. According to the narrow band imaging method, a lesion site in the mucous membrane surface layer of the living body can be more accurately discovered. As for such observation methods in the endoscope apparatus, there is a demand to achieve observation by switching between the white light imaging method and the narrow band imaging method.

A light receiving surface of an image sensor, in which an image is to be captured by a single-plate image sensor, is provided a color filter in order to generate and display a color image by the above-described observation methods. In the color filter, filters that pass light of red (R), green (G), green (G), and blue (B) wavelength bands are arrayed as one filter unit (unit) per pixel, and the array is generally so-called Bayer array. In this case, each pixel receives light of a wavelength band having passed through the filter, and the image sensor generates an electric signal of a color component corresponding to the light of the wavelength band. Therefore, interpolation processing to interpolate a signal value of a color component that has not passed through the filter and is missing is performed in each pixel in processing to generate a color image. Such interpolation processing is called demosaicing processing (refer to Japanese Laid-open Patent Publication No. 8-237672, for example).

Electric signals generated by an image sensor provided with the color filter may have different gain between color components due to differences in transmission characteristics of the filters and the like. Therefore, the gain of the electric signals of the respective color components are adjusted between the color components at the time of generating a color image signal based on the electric signals of the respective color components of red, green, and blue. A color image expressing colors of the subject can be obtained by generating the color image signal by applying the demosaicing processing using the electric signals having the gain adjusted.

SUMMARY

In some embodiments, an endoscope apparatus includes: a light source unit configured to emit white illumination light including red wavelength band light, green wavelength band light, and blue wavelength band light, or to emit narrow-band illumination light including narrow band light included in each of blue and green wavelength bands; an image sensor having a plurality of pixels arranged in a lattice pattern, each of which is configured to receive light, the image sensor being configured to perform photoelectric conversion on the light received by each of the plurality of pixels to generate an electric signal; a color filter comprising a filter unit arranged correspondingly to the plurality of pixels, the filter unit including a plurality of filters having a filter for passing the blue wavelength band light, a filter for passing the blue wavelength band light and the green wavelength band light, and a filter for passing at least the red wavelength band light, or the filter unit including a plurality of filters having a filter for passing the blue wavelength band light, a filter for passing the blue wavelength band light and the red wavelength band light, and a filter for passing at least the green wavelength band light, the number of filters for passing the green wavelength band light being half or more of the number of all the filters of the filter unit, and the number of filters for passing the blue wavelength band light being equal to or more than the number of filters for passing the green wavelength band light; a first gain adjustment unit configured to adjust a gain of the electric signal generated by the image sensor based on the light received by each of the plurality of pixels via the color filter; a demosaicing processing unit configured to generate image signals of color components respectively that pass through the filter unit based on the electric signal whose gain has been adjusted by the first gain adjustment unit; a color conversion processing unit configured to separate color components from an image signal having a blue component and at least one of a green component or a red component out of the image signals generated by the demosaicing processing unit to obtain an image signal of the green component or the red component when the light source unit emits the white illumination light, and configured to generate image signals of the blue component, the green component, and the red component, respectively; and a second gain adjustment unit configured to adjust a gain of at least part of the image signals of the blue component, the green component, and the red component generated by the color conversion processing unit.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 3 is a schematic diagram illustrating a structure of a pixel according to the embodiment of the present invention;

FIG. 4 is a schematic diagram illustrating an exemplary structure of a color filter according to the embodiment of the present invention;

FIG. 9 is a schematic diagram illustrating a structure of a color filter according to a second modified example of the embodiment of the present invention;

FIG. 10 is a schematic diagram illustrating a structure of a color filter according to a third modified example of the embodiment of the present invention;

FIG. 11 is a schematic diagram illustrating a structure of a color filter according to a fourth modified example of the embodiment of the present invention; and FIG. 12 is a schematic diagram illustrating a structure of a color filter according to a fifth modified example of the embodiment of the present invention.

DETAILED DESCRIPTION

Modes for carrying out the present invention (hereinafter referred to as "embodiment(s)") will be described below. In some embodiments, a medical endoscope apparatus that captures and displays an image inside a body cavity of a subject such as a patient will be described. Note that the present invention is not limited by the embodiments. The same reference signs are used to designate the same elements throughout the drawings.

Figure 1:
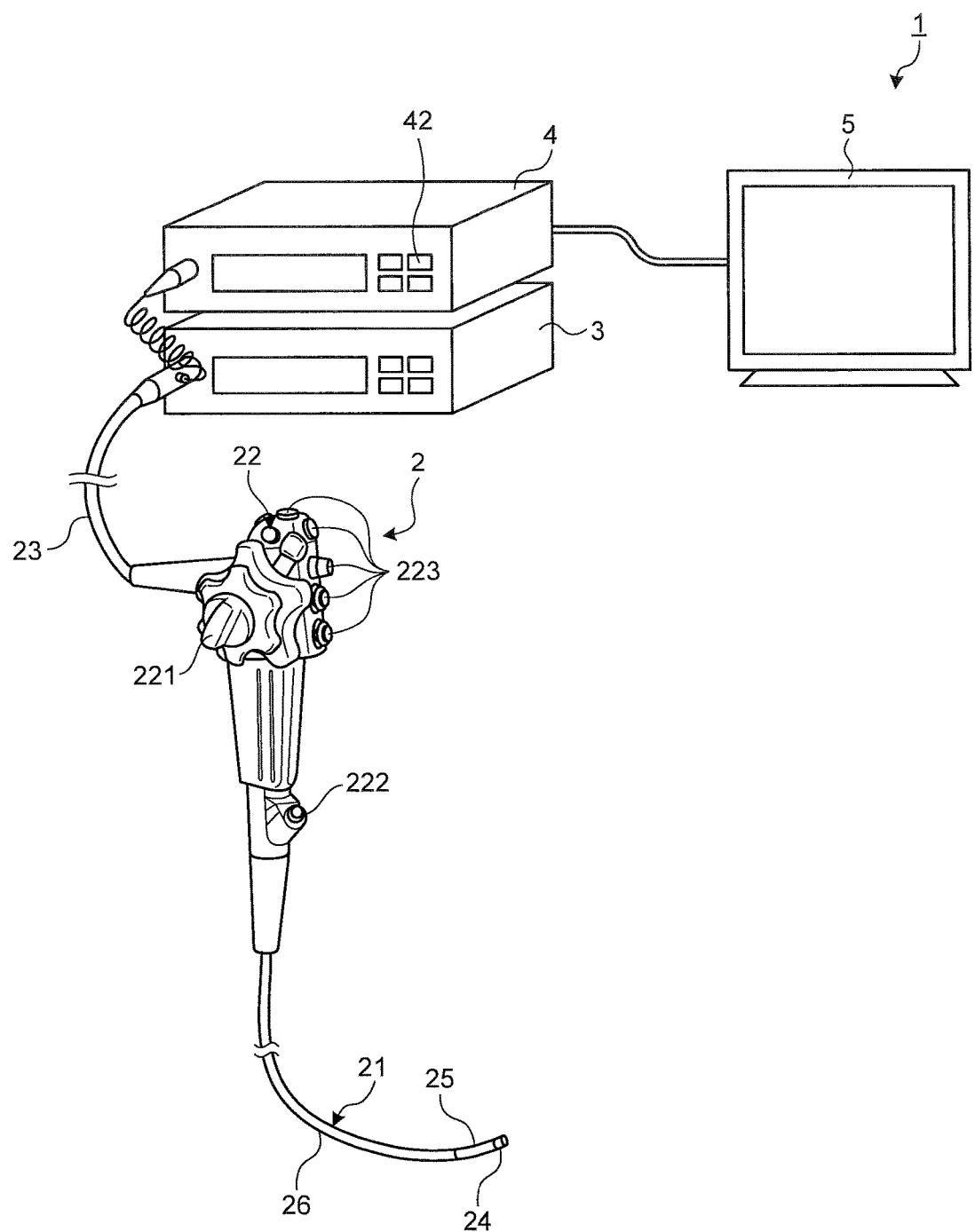
FIG. 1 is a diagram illustrating a general structure of an endoscope apparatus according to an embodiment of the present invention.
Figure 2:
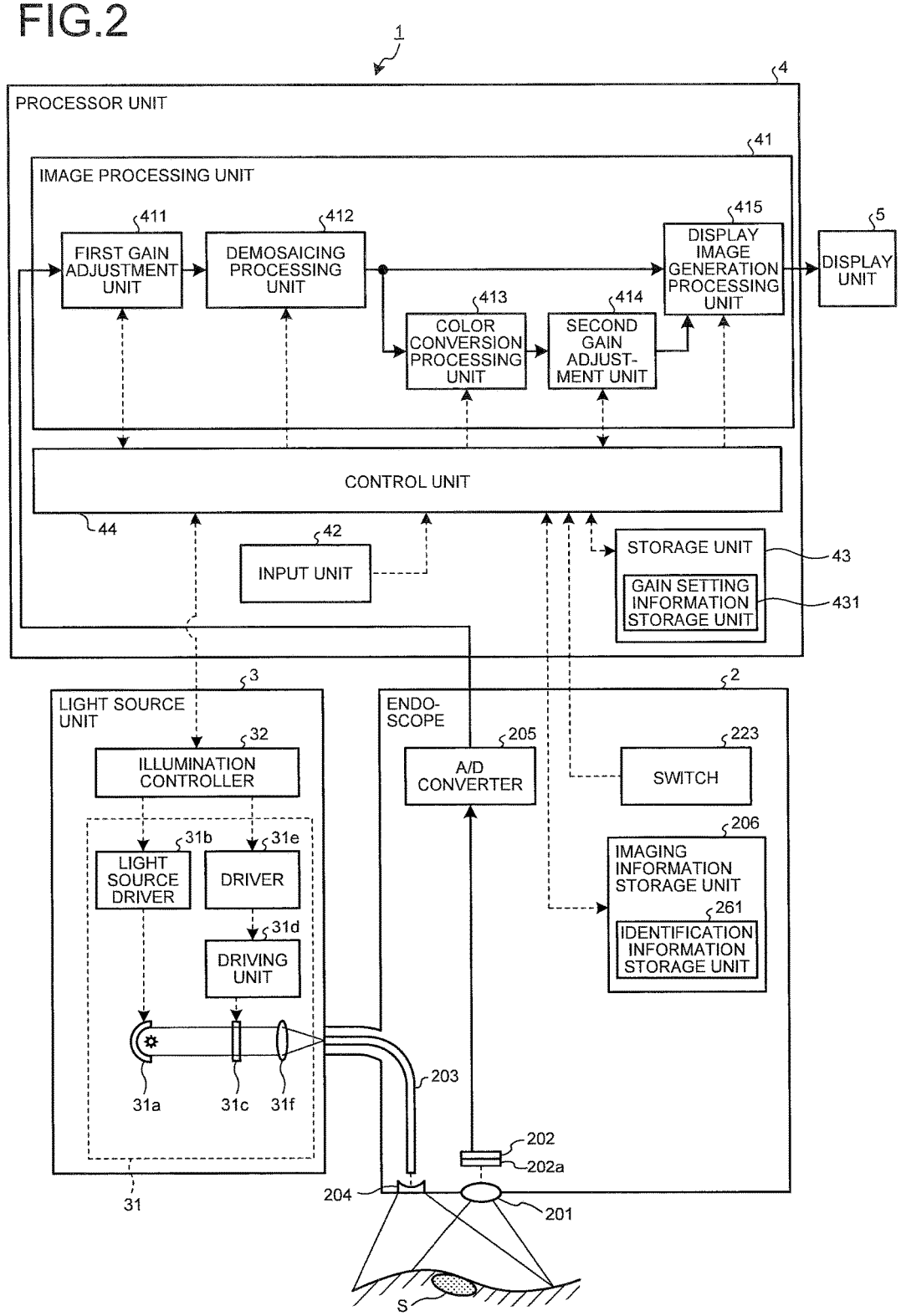
FIG. 2 is a schematic diagram illustrating the endoscope apparatus according the embodiment of the present invention.

FIG. 1 is a diagram illustrating a general structure of an endoscope apparatus according to an embodiment of the present invention. FIG. 2 is a schematic diagram illustrating the endoscope apparatus according the embodiment. An endoscope apparatus 1 illustrated in FIGS. 1 and 2 includes: an endoscope 2 that captures an in-vivo image of an observed region by inserting an insertion portion 21 into a body cavity of a subject and generates an electric signal; a light source unit 3 that generates illumination light to be emitted from a distal end of the endoscope 2; a processor unit 4 that performs predetermined image processing on the electric signal obtained by the endoscope 2 and further integrally controls operation of the entire endoscope apparatus 1; and a display unit 5 that displays the in-vivo image having been subjected to the image processing by the processor unit 4. The endoscope apparatus 1 inserts the insertion portion 21 into the body cavity of the subject such as a patient, and captures the in-vivo image inside the body cavity. A user such as a doctor observes the captured in-vivo image, thereby examining existence of a bleeding site or a tumor site (lesion site S) that is a detection target region.

The endoscope 2 includes: the insertion portion 21 having flexibility and formed in a thin long shape; an operating unit 22 connected to a proximal end of the insertion portion 21 and receiving input of various kinds of operation signals, and a universal cord 23 extending from the operating unit 22 in a direction different from an extending direction of the insertion portion 21 and including various kinds of cables to connect the light source unit 3 and the processor unit 4.

The insertion portion 21 includes a distal end portion 24 including an image sensor 202 in which pixels (photodiodes) to receive light are arrayed in a lattice (matrix) pattern and an image signal is generated by performing photoelectric conversion to the light received by the pixel; a bending portion 25 that is formed of a plurality of bending pieces and can be freely bent; and a flexible tube portion 26 connected to a proximal end side of the bending portion 25, having flexibility, and formed in a long shape.

The operating unit 22 includes: a bending knob 221 to bend the bending portion 25 in a vertical direction and a horizontal direction; a treatment tool insertion portion 222 to insert a treatment tool such as a living body forceps, an electrical scalpel, or a test probe into the body cavity of the subject; and a plurality of switches 223 to receive command signal to make the light source unit 3 perform illumination light switching operation, an operation command signal for an external device that connects the treatment tool and the processor unit 4, a water feed command signal to feed water, a suction command signal to perform suctioning, and the like. The treatment tool to be inserted from the treatment tool insertion portion 222 is exposed from an opening (not illustrated) via a treatment tool channel (not illustrated) provided at a distal end of the distal end portion 24.

The universal cord 23 includes at least a light guide 203 and a cable assembly formed by assembling one or a plurality of signal lines. The cable assembly corresponds to the signal lines to transmit and receive signals between the endoscope 2, light source unit 3, and processor unit 4, and includes a signal line to transmit and receive setting data, a signal line to transmit and receive an image signal, a signal line to transmit and receive a drive timing signal to drive the image sensor 202, and the like.

Further, the endoscope 2 includes an imaging optical system 201, the image sensor 202, the light guide 203, an illumination lens 204, an A/D converter 205, and an imaging information storage unit 206.

The imaging optical system 201 is provided at the distal end portion 24 and collects light at least from an observed region. The imaging optical system 201 is formed by using one or a plurality of lenses. The imaging optical system 201 may be provided with an optical zooming mechanism to change a viewing angle and a focusing mechanism to change a focal point.

The image sensor 202 is disposed vertically to an optical axis of the imaging optical system 201 and generates an electric signal (image signal) by photoelectrically converting an optical image formed by the imaging optical system 201. The image sensor 202 is implemented by a charge coupled device (CCD) image sensor, a complementary metal oxide semiconductor (CMOS) image sensor, and the like.

FIG. 3 is a schematic diagram illustrating a structure of a pixel of the image sensor according to the embodiment. In the image sensor 202, a plurality of pixels that receives the light from the imaging optical system 201 is arrayed in a lattice (matrix) pattern. Further, the image sensor 202 generates an electric signal (also referred to as image signal) by performing photoelectric conversion on the light received by each of the pixels. This electric signal includes a pixel value (luminance value) of each of the pixels, pixel positional information, and the like. In FIG. 3, a pixel arranged in a $i^{th}$ row and a $j^{th}$ column is indicated as a pixel $P_{ij}$.

The image sensor 202 includes a color filter 202a provided between the imaging optical system 201 and the image sensor 202 and including a plurality of filters each passing light of a wavelength band individually set. The color filter 202a is provided on a light receiving surface of the image sensor 202.

FIG. 4 is a schematic diagram illustrating an exemplary structure of the color filter according to the embodiment. In the embodiment, for example, the color filter 202a is formed by two-dimensionally arranging filter units U1 (in a matrix form) in accordance with arrangement of pixels $P_{ij}$, and the filter unit U1 includes four filters arranged in a 2×2 matrix. The pixel $P_{ij}$ provided with a filter receives light of a wavelength band passed through the filter. For example, the pixel $P_{ij}$ provided with a filter that passes light of a blue wavelength band receives the light of the blue wavelength band. In the following, the pixel $P_{ij}$ that receives the light of the blue wavelength band will be referred to as a B pixel. In the same manner, a pixel that receives light of a green wavelength band will be referred to as a G pixel, and a pixel that receives light of a red wavelength band will be referred to as an R pixel.

Here, the filter unit U1 passes light of a blue (B) wavelength band $H_B$, light of a green (G) wavelength band $H_G$, and light of a red (R) wavelength band $H_R$. Additionally, in the filter unit U1, a plurality of filters is selected and arranged such that the number of filters for passing the light of wavelength band $H_G$ is half or more of the number of all filters constituting the filter unit U1 and further the number of filters for passing the light of wavelength band $H_B$ is equal to or more than the number of filters for passing the light of the wavelength band $H_G$. For example, the blue, green, and red wavelength bands $H_B$, $H_G$, $H_R$ have following wavelengths: the wavelength band $H_B$ is 390 nm to 500 nm, the wavelength band $H_G$ is 500 nm to 600 nm, and the wavelength band $H_R$ is 600 nm to 700 nm.

As illustrated in FIG. 4, the filter unit U1 according to the embodiment is formed of one B filter that passes the light of wavelength band $H_B$, two G filters each of which passes the light of the wavelength band $H_G$, and one Mg filter that passes light of the wavelength band $H_B$ and light of the wavelength band $H_R$. In the following, in the case where the B filter is provided at a position corresponding to the pixel $P_{ij}$, the B filter will be indicated as $B_{ij}$. In the same manner, in the case where the G filter is provided at the position corresponding to the pixel $P_{ij}$, the G filter will be indicated as $G_{ij}$, and in the case where the Mg filter is provided there, the Mg filter will be indicated as $Mg_{ij}$. In the case of mixing the light of the wavelength band $H_B$ (blue light) with the light of the wavelength band $H_R$ (red light), the light becomes magenta (Mg).

In the filter unit U1, the number of the filters for passing light of the wavelength band $H_G$ (G filter) is two, and the number of the filters (B filter and Mg filter) for passing light of the wavelength band $H_B$ is two.

Figure 5:
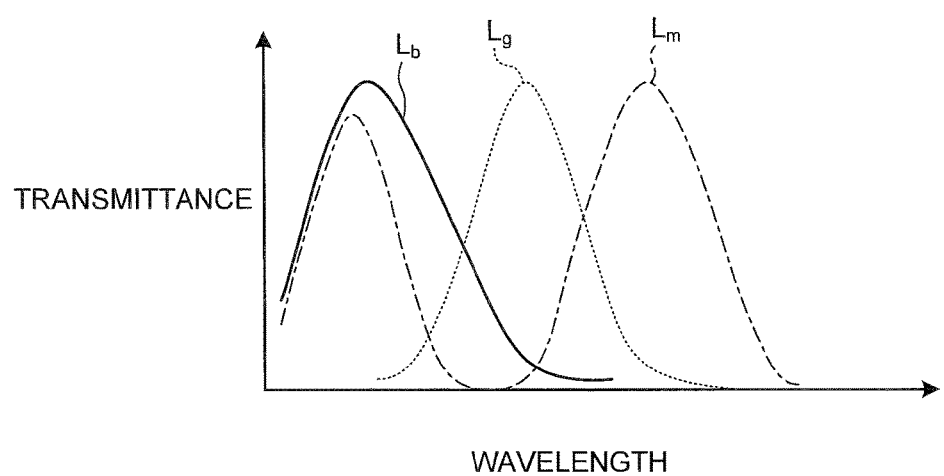
FIG. 5 is a diagram illustrating exemplary characteristics of respective filters in the color filter according to the embodiment of the present invention.

FIG. 5 is a diagram illustrating exemplary characteristics of the respective filters in the color filter according to the embodiment, and illustrates a relation between a light wavelength and transmittance of each filter. In FIG. 5, a transmittance curve is normalized such that maximum values of the transmittance of the filters are identical. A curve $L_b$ (solid line) illustrated in FIG. 5 represents a transmittance curve of the B filter, a curve $L_g$ (dotted line) represents a transmittance curve of the G filter, and a curve $L_m$ (dot-and-dash line) represents a transmittance curve of the Mg filter.

The B filter passes the light of the wavelength band $H_B$. The Mg filter passes light of a wavelength band of magenta that is a complementary color of green. In other words, the Mg filter absorbs the light of the wavelength band $H_G$ and passes the light of wavelength band $H_B$, and further passes the light of the wavelength band $H_R$. The G filter passes the light of the wavelength band $H_G$. Note that in the present specification the complementary color is a color formed by light including at least two wavelength bands out of the wavelength bands $H_B$, $H_G$, $H_R$.

Referring back to FIGS. 1 and 2, the light guide 203 is formed by using glass fibers and the like, and forms a light guide path of the light emitted from the light source unit 3.

The illumination lens 204 is provided at a distal end of the light guide 203, and emits the light to the outside of the distal end portion 24 while diffusing the light guided by the light guide 203.

The A/D converter 205 performs A/D conversion on the electric signal generated by the image sensor 202, and outputs the converted electric signal to the processor unit 4.

The imaging information storage unit 206 stores various kinds of programs to operate the endoscope 2, and data including various kinds of parameters needed to operate the endoscope 2, identification information of the endoscope 2, and the like. Further, the imaging information storage unit 206 includes an identification information storage unit 261 to store the identification information. The identification information includes unique information (ID) of the endoscope 2, model year, specification information, transmission method, array information of the filters relative to the color filter 202a, and the like. The imaging information storage unit 206 is implemented by using a flash memory and the like.

Next, a configuration of the light source unit 3 will be described. The light source unit 3 includes an illumination unit 31 and an illumination controller 32.

The illumination unit 31 emits a plurality of rays of illumination light of the wavelength bands different from one another in a switching manner under control of the illumination controller 32. The illumination unit 31 includes a light source 31a, a light source driver 31b, a switch filter 31c, a driving unit 31d, a driver 31e, and a condenser lens 31f.

The light source 31a emits white illumination light including light of red wavelength band $H_R$, light of green wavelength band $H_G$, and light of blue wavelength band $H_B$ under the control of the illumination controller 32. The white illumination light generated by the light source 31a is emitted to the outside from the distal end portion 24 via the switch filter 31c, condenser lens 31f, and light guide 203. The light source 31a is implemented by using a light source such as a white LED and a xenon lamp that emits a white light.

The light source driver 31b makes the light source 31a emit the white illumination light by supplying current to the light source 31a under the control of the illumination controller 32.

The switch filter 31c only passes blue narrow-band light and green narrow-band light out of the white illumination light emitted from the light source 31a. The switch filter 31c is disposed in a manner insertable and removable on an optical path of the white illumination light emitted from the light source 31a under the control of the illumination controller 32. The switch filter 31c is disposed on the optical path of the white illumination light, thereby passing only the two kinds of narrow-band light. More specifically, the switch filter 31c passes a narrow-band illumination light including light of a narrow band $T_B$ (e.g., 390 nm to 445 nm) in the wavelength band $H_B$ and light of a narrow band $T_G$ (e.g., 530 nm to 550 nm) in the wavelength band $H_G$. The narrow bands $T_B$, $T_G$ are the wavelength bands of the blue light and the green light which are easily absorbed by hemoglobin inside the blood. Preferably, the narrow band $T_B$ includes at least the wavelength band of 405 nm to 425 nm. The light emitted limitedly from this band is called the narrow-band illumination light, and observing an image with this narrow-band illumination light is referred to as a narrow band imaging (NBI) method. In the embodiment, the configuration of switching between the white illumination light and the narrow-band light by the switch filter is provided, but the present invention is not limited thereto. For example, it is also possible to have a configuration of switching between a light source emitting the white illumination light and a laser light source emitting a narrow-band light. Alternatively, it is also possible to have a configuration of switching between pseudo white light generated by simultaneous light emission from a plurality of laser light sources for emitting rays of light of different wavelength bands and a narrow-band light emitting light of a part of the wavelength bands thereof. Further, the present invention is applicable to a method other than NBI method (using the above $T_B$ and $T_G$ as the narrow bands) and also applicable to, for example, a configuration of switching between the white light and a special light of a narrow band out of the wavelength band other than $T_B$ and $T_G$.

The driving unit 31d is formed by using a stepping motor, a DC motor, or the like, and causes the switch filter 31c to be inserted into or removed from the optical path of the light source 31a.

The driver 31e supplies predetermined current to the driving unit 31d under the control of the illumination controller 32.

The condenser lens 31f condenses the white illumination light emitted from the light source 31a or the narrow-band illumination light having passed through the switch filter 31c, and emits the light to the outside of the light source unit 3 (light guide 203).

The illumination controller 32 turns on/off the light source 31a by controlling the light source driver 31b, and inserts or removes the switch filter 31c relative to the optical path of the light source 31a by controlling the driver 31e, thereby controlling a kind (band) of illumination light emitted from the illumination unit 31.

More specifically, the illumination controller 32 controls the illumination light emitted from the illumination unit 31 to be switched between the white illumination light and the narrow-band illumination light by inserting or removing the switch filter 31c relative to the optical path of the light source 31a. In other words, the illumination controller 32 controls switching between the white light imaging (WLI) method using the white illumination light including the light of the wavelength bands $H_B$, $H_G$, $H_R$ and the narrow band imaging (NBI) method using the narrow-band illumination light formed of light of the narrow bands $T_B$, $T_G$.

Next, a configuration of the processor unit 4 will be described. The processor unit 4 includes an image processing unit 41, an input unit 42, a storage unit 43, and a control unit 44.

The image processing unit 41 executes predetermined image processing based on an electric signal received from the endoscope 2 (A/D converter 205) and generates image information (display image signal) displayed by the display unit 5. The image processing unit 41 includes a first gain adjustment unit 411, a demosaicing processing unit 412, a color conversion processing unit 413, a second gain adjustment unit 414, and a display image generation processing unit 415.

The first gain adjustment unit 411 adjusts a gain of each of an electric signal of a blue component (B signal), an electric signal of a green component (G signal), and an electric signal of a magenta color component (Mg signal) relative to the electric signal output from the endoscope 2 after A/D conversion. More specifically, the first gain adjustment unit 411 detects the B signal, G signal, and Mg signal generated by the image sensor 202 based on the light received in the pixel $P_{ij}$ via the color filter 202a, and outputs the detection signals to the control unit 44. Upon receipt of a control signal in accordance with a detection result from the control unit 44, the first gain adjustment unit 411 sets any one of the B signal, G signal, and Mg signal as a reference, and adjusts a gain of a signal other than the signal set as the reference.

The demosaicing processing unit 412 discriminates an interpolation direction based on correlation of the color information (pixel values) of a plurality of pixels, and generates a color image signal by performing interpolation based on the color information of the pixels arrayed in the discriminated interpolation direction.

For example, the demosaicing processing unit 412 discriminates the interpolation direction of an interpolation target pixel (pixel other than a luminance component pixel) by using a pixel value of a pixel set as the luminance component pixel, and interpolates the luminance component in the pixel other than the luminance component pixel based on the discriminated interpolation direction, and further generates an image signal constituting a single image in which each of the pixels has the pixel value of the luminance component or an interpolated pixel value (hereinafter referred to as interpolation value). If the observation method is the white light imaging (WLI) method, the demosaicing processing unit 412 selects a green component as the luminance component. In the case of the narrow band imaging (NBI) method, the demosaicing processing unit 412 selects a blue component as the luminance component. If the observation method is the white light imaging (WLI) method and the G pixel is selected as the luminance component pixel, the demosaicing processing unit 412 interpolates, by using a pixel value of the G pixel, green components in the B pixel that receives the light of the blue wavelength band and in the Mg pixel that receives the light of the magenta wavelength band.

After that, the demosaicing processing unit 412 generates an image signal of a color component other than the luminance component based on the pixel value of the luminance component, the interpolation value, and the pixel value of the pixel other than the luminance component pixel. For example, in the case where the luminance component pixel is the G pixel, the demosaicing processing unit 412 generates, per color component, an image signal constituting the image provided with the pixel values of the blue component and the magenta color component or the interpolation value by using the pixel value of the G pixel, the interpolation value, and the pixel values of the B pixel and the Mg pixel.

The demosaicing processing unit 412 generates a color image signal constituting a color image by using the respective image signals of the green component, blue component, and magenta color component.

The color conversion processing unit 413 performs color separation processing for a complementary color in the case where the complementary color exists in the light passed through the color filter 202a. More specifically, since magenta exists in the embodiment, an electric signal of the red component (R signal) is separated by subtracting the blue component from the color components of the magenta in the case of the white light imaging method.

The second gain adjustment unit 414 adjusts a gain of each of the R signal, G signal, and B signal output from the color conversion processing unit 413. More specifically, the second gain adjustment unit 414 detects the B signal, G signal, and R signal output from the color conversion processing unit 413, and outputs the detection signals to the control unit 44. Upon receipt of a control signal in accordance with a detection result from the control unit 44, the second gain adjustment unit 414 sets any one of the B signal, G signal, and R signal as a reference, and adjusts a gain of a signal other than the signal set as the reference.

The display image generation processing unit 415 performs, on the electric signal generated by the demosaicing processing unit 412 or the second gain adjustment unit 414, gray scale conversion, enlargement processing, or structure emphasizing processing on structures such as capillary vessels and microscopic patterns of a mucosa in a mucous membrane surface layer. After performing the predetermined processing, the display image generation processing unit 415 outputs the electric signal to the display unit 5 as a display image signal for display.

The image processing unit 41 executes OB clamp processing and the like in addition to the above-described demosaicing processing. In the OB clamp processing, processing for correcting an offset amount of a black level is performed on the electric signal input from the distal end portion 24 (A/D converter 205).

The input unit 42 is an interface for a user to input into the processor unit 4, and formed by including a power switch to turn on/off a power source, a mode switch button to switch an imaging mode and other kinds of modes, an illumination light switch button to switch the illumination light of the light source unit 3, and the like.

The storage unit 43 records various kinds of programs to operate the endoscope apparatus 1 and data including various kinds of parameters, and the like needed to operate the endoscope apparatus 1. Further, the storage unit 43 includes a gain setting information storage unit 431 to store gain setting information for gain adjustment processing executed by the first gain adjustment unit 411 and the second gain adjustment unit 414 (for example, setting information of a reference pixel, a gain coefficient related to gain adjustment or a calculation program for the gain coefficient). The storage unit 43 may also store information related to the endoscope 2 such as a relation table between unique information (ID) of the endoscope 2 and information related to filter arrangement in the color filter 202*a*. The storage unit 43 is implemented by using a semiconductor memory such as a flash memory and a dynamic random access memory (DRAM).

The control unit 44 is formed by using a CPU or the like, and performs drive control for the respective units including the endoscope 2 and the light source unit 3, and information input/output control relative to the respective units. The control unit 44 transmits, to the endoscope 2, setting data for imaging control recorded in the storage unit 43 (e.g., a reading target pixel), a timing signal related to imaging timing, and the like via a predetermined signal line. The control unit 44 outputs color filter information (identification information) obtained via the imaging information storage unit 206 to the image processing unit 41, and further outputs information related to arrangement of the switch filter 31*c* to the light source unit 3 based on the color filter information.

Further, upon receipt of the detection signals from the first gain adjustment unit 411 and the second gain adjustment unit 414, the control unit 44 generates setting information for the gain adjustment (reference pixel setting, positional information of the reference pixel in the color filter 202*a*, and a gain coefficient) by referring to the gain setting information and the identification information, and outputs a control signal corresponding to the setting information to the first gain adjustment unit 411 and the second gain adjustment unit 414.

Next, the display unit 5 will be described. The display unit 5 receives the display image signal generated by the processor unit 4 via a video cable and displays the in-vivo image corresponding to the display image signal. The display unit 5 is formed by using liquid crystal or organic electro-luminescence (EL).

Figure 6:
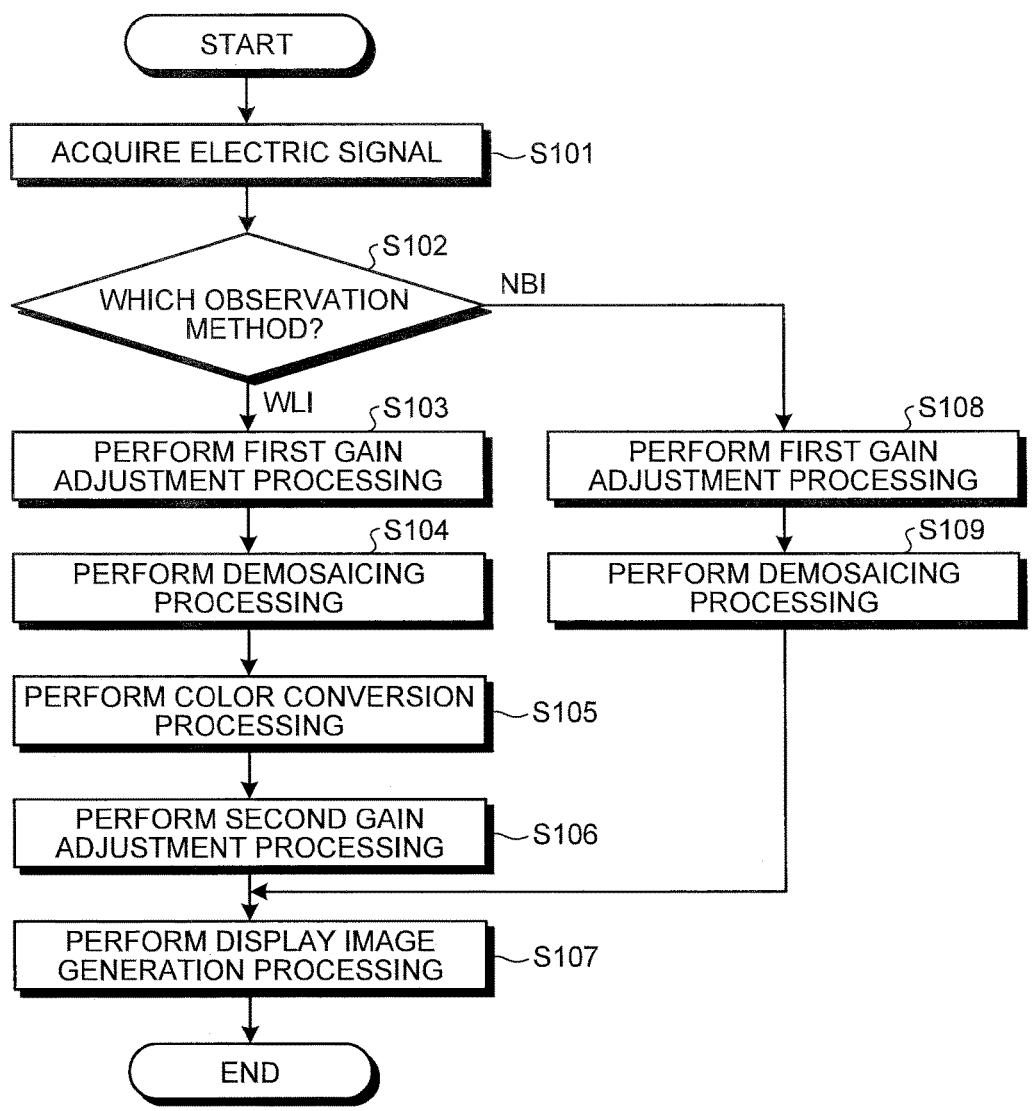
FIG. 6 is a flowchart illustrating signal processing executed by a processor unit of the endoscope apparatus according to the embodiment of the present invention.

FIG. 6 is a flowchart illustrating signal processing executed by the processor unit of the endoscope apparatus according to the embodiment. The processor unit 4 acquires an electric signal from the endoscope 2 and outputs the electric signal to the demosaicing processing unit 412 (Step S101). The electric signal from the endoscope 2 is a signal generated by the image sensor 202 and including Raw image data converted to a digital signal by the A/D converter 205.

When the electric signal is received in the image processing unit 41, the image processing unit 41 determines which of the white light imaging (WLI) method and the narrow band imaging (NBI) method is used to generate the received electric signal based on the control signal from the control unit 44 (for example, information related to the illumination light and information indicating the observation method) (Step S102).

If the observation method is the white light imaging method (Step S102: WLI), the first gain adjustment unit 411 adjusts a gain of each of the B signal, G signal, and Mg signal (first gain adjustment), and outputs the adjusted signals to the demosaicing processing unit 412 (Step S103).

More specifically, the first gain adjustment unit 411 detects the B signal, G signal, and Mg signal from the received electric signal and outputs the detected results to the control unit 44 as the detection signals. Upon receipt of the detection signal, the control unit 44 refers to the gain setting information and determines gain setting corresponding to filter array (for example, reference pixel setting and the gain coefficient) based on the observation method information determined in Step S102, and outputs the determination result and setting as the control signal.

Upon receipt of the control signal from the control unit 44, the first gain adjustment unit 411 adjusts the gain of the B signal, G signal, and Mg signal in accordance with the control signal. For example, in the case where the G signal is set as the reference, the first gain adjustment unit 411 multiplies the gain coefficient (based on the gain setting information) by the B signal and the Mg signal.

The above-described gain adjustment is generally called white balance adjustment. Here, the above-described gain coefficient in the endoscope apparatus 1 (coefficient for white balance adjustment=white balance coefficient) is obtained as, for example, the gain setting information in the embodiment by preliminarily imaging a white subject and calculating a gain coefficient in which pixel signal values of the respective colors obtained at the time of imaging become equal. Therefore, the above-described gain adjustment is to multiply the gain coefficient thus preliminarily set so as to conform to the reference color signal.

When the electric signals (B signal, G signal, and Mg signal) having the gain adjusted by the first gain adjustment unit 411 are received in the demosaicing processing unit 412, the demosaicing processing unit 412 performs demosaicing processing based on the electric signals (Step S104).

The demosaicing processing unit 412 discriminates the interpolation direction of an interpolation target pixel (pixel other than a luminance component pixel) by using, for example, a pixel value of a pixel set as the luminance component pixel, and interpolates the luminance component in the pixel other than the luminance component pixel based on the discriminated interpolation direction, and further generates an image signal constituting a single image in which each of the pixels has the pixel value or the interpolation value of the luminance component. After that, the demosaicing processing unit 412 generates, per color component, an image signal constituting a single image having a pixel value of the color component other than the luminance component or the interpolation value based on the pixel value of the luminance component, the interpolation value, and the pixel value of the pixel other than the luminance component pixel. After generating the image signal per color component, the demosaicing processing unit 412 generates a color image signal constituting a color image by using the respective image signals of the green component, blue component, and magenta color component.

After the color image signal is generated by the demosaicing processing unit 412, the color conversion processing unit 413 performs color conversion processing including color separation processing for a complementary color (Step S105). More specifically, the color conversion processing unit 413 separates the red component (R signal) by subtracting the blue component out of the magenta color component of the Mg signal. In other words, components corresponding to three original colors are extracted from the color components included in the complementary color.

After the color separation processing for the complementary color is performed by the color conversion processing unit 413, the second gain adjustment unit 414 adjusts a gain of each of the B signal, G signal, and R signal relative to the electric signal after the color separation processing (second gain adjustment processing), and outputs the adjusted electric signal to the display image generation processing unit 415 (Step S106).

More specifically, the second gain adjustment unit 414 first detects the B signal, G signal, and R signal from the received electric signal, and outputs the detection result to the control unit 44. Upon receipt of the detection result, the control unit 44 refers to the gain setting information and determines gain setting (for example, reference pixel setting and the gain coefficient) based on the observation method information determined in Step S102, and outputs the determination result and setting as the control signal.

Upon receipt of the control signal from the control unit 44 corresponding to the detection result, the second gain adjustment unit 414 adjusts the gain of the B signal, G signal, and R signal in accordance with the control signal. The second gain adjustment unit 414 multiplies the gain coefficient by the B signal and the R signal by setting the G signal as the reference, for example. This gain coefficient is based on the same idea as the above-described first gain adjustment processing. In the embodiment, only gain of the R signal is adjusted in Step S106 because the gain of the B signal is adjusted in Step S103. Further, in the second gain adjustment unit 414, gain adjustment for the B signal, G signal, and R signal may be performed while setting the gain coefficients of the B signal and the G signal as 1.

The display image generation processing unit 415 generates a display image signal for display by applying gray scale conversion, enlargement processing, and the like to the electric signals (B signal, G signal, and R signal) having the gain adjusted by the second gain adjustment unit 414 (Step S107). After applying the predetermined processing, the display image generation processing unit 415 outputs the electric signal to the display unit 5 as a display image signal.

On the other hand, if the observation method is determined to be the narrow band imaging method by the image processing unit 41 in Step S102 (Step S102: NBI), the first gain adjustment unit 411 adjusts the gain of the B signal, G signal, and Mg signal (first gain adjustment processing), and outputs the electric signal as adjusted to the demosaicing processing unit 412 (Step S108).

Here, in the case of the narrow band imaging method, the light of the wavelength band $H_R$ is not included in the narrow-band illumination light. Therefore, the Mg filter passes only the light of the narrow band $T_B$, and the Mg pixel provided with the Mg filter substantially functions as the B pixel.

The first gain adjustment unit 411 first detects the received B signal, G signal, and Mg signal (B signal) from the received electric signal, and outputs a detected detection signals to the control unit 44. Upon receipt of the detection signals, the control unit 44 refers to the gain setting information and determines gain setting corresponding to the filter array (for example, reference pixel setting and gain coefficient) based on the observation method information determined in Step S102, and outputs the determination result and setting information as the control signal.

Upon receipt of the control signal from the control unit 44, the first gain adjustment unit 411 adjusts the gain of the B signal and G signal in accordance with the control signal. For example, in the case where the G signal is set as the reference as the gain setting information, the first gain adjustment unit 411 multiplies the gain coefficient by the B signal (and Mg signal).

When the electric signals having the gain adjusted by the first gain adjustment unit 411 are received in the demosaicing processing unit 412, the demosaicing processing unit 412 performs the demosaicing processing based on the electric signals (Step S109). The demosaicing processing unit 412 performs interpolation processing on the green component and the blue component respectively by the same processing as above-described Step S104, and generates, per color component, the image signal constituting a single image in which each of the pixels includes the pixel value or the interpolation value. The demosaicing processing unit 412 generates a color image signal constituting a color image by using the respective image signals of the green component and the blue component (including the blue component obtained from the Mg pixel).

After generating the color image signal by the processing in Step S109, the control unit 44 proceeds to Step S107 and makes the display image generation processing unit 415 generate a display image signal (Step S107). The display image generation processing unit 415 performs gray scale conversion, enlargement processing, and the like on the color image signal generated by the demosaicing processing unit 412 in Step S109, and generates a display image signal for display. After applying the predetermined processing, the display image generation processing unit 415 outputs the electric signal to the display unit 5 as a display image signal.

According to the above-described embodiment, provided are: the light source unit 3 that emits the white illumination light or the narrow-band illumination light as the illumination light; the image sensor 202 formed by arraying the plurality of pixels; the color filter 202a including the plurality of filters where the filters that pass the light of wavelength bands $H_B$, $H_G$ are arrayed under the predetermined conditions; the first gain adjustment unit 411 that adjusts a gain of each of the B signal, G signal, and Mg signal; the demosaicing processing unit 412 that applies interpolation processing to interpolate the luminance component based on the electric signals, and generates the color image; the color conversion processing unit 413 that performs color separation processing for the complementary color in the case where the illumination light is the white illumination light; and the second gain adjustment unit 414 that adjusts a gain of each of the B signal, G signal, and R signal. The first gain adjustment unit 411 adjusts the gain of the signal of each color including the complementary color (magenta), and the demosaicing processing unit 412 performs demosaicing processing by using the signals having the gain adjusted by the first gain adjustment unit 411. Further, in the case of the white light imaging method, the second gain adjustment unit 414 adjusts the gain of each of the RGB signals having been subjected to color separation processing for the complementary color by the color conversion processing unit 413. In the embodiment, the complementary color pixel such as the Mg pixel that receives the light of the blue wavelength band is included. Therefore, high resolution of the luminance component can be achieved by a signal of a color component obtained by the complementary color pixel in both of the white light imaging using the green component as the luminance component and the narrow band imaging using the blue component as the luminance component. More specifically, in the filter unit U1 formed of the four filters illustrated in FIG. 4, the G signals of two pixels (signal of the luminance component at the time of performing the white light imaging) can be obtained by the two G pixels at the time of performing the white light imaging, and further the B signals of two pixels (signal of the luminance component at the time of performing the narrow band imaging) can be obtained by the one B pixel and the one Mg pixel at the time of performing the narrow band imaging. Further, in the embodiment, interpolation is performed by using the color correlation between the respective color signals by performing the gain adjustment (white balance) for the B signal, G signal, and Mg signal by the first gain adjustment unit 411 before demosaicing. Therefore, the demosaicing processing can be performed while keeping sense of resolution. With this configuration, a high-resolution image can be obtained under both of the white light imaging method and the narrow band imaging method.

Further, according to the above-described embodiment, the first gain adjustment unit 411 adjusts the gain of the B signal, G signal, and Mg signal generated by the image sensor 202 while the second gain adjustment unit 414 adjusts the gain of each of the B signal, G signal, and R signal having been subjected to the color separation processing for the complementary color by the color conversion processing unit 413. Therefore, white balance for demosaicing and white balance for display image generation can be independently performed, and white balance adjustment suitable for the respective processing can be performed.

Further, according to the above-described embodiment, the image processing unit 41 obtains the positional information of the pixel set as the reference pixel relative to gain adjustment based on the identification information (information of the color filter 202$a$) from the control unit 44. Therefore, even in the case of replacing the endoscope 2 (distal end portion 24) connected to the processor unit 4 with an endoscope 2 having a distal end portion 24 provided with different filter arrangement in the color filter 202$a$, the positional information of the set reference pixel can be correctly specified.

In the above-described embodiment, it has been described that the second gain adjustment unit 414 performs gain adjustment such that the gain of the B signal and the R signal become equal by setting the gain of the G signal as the reference. However, gain adjustment may also be performed such that the gain of the G signal and B signal become equal by setting the gain of the Mg signal as the reference. In the second gain adjustment processing, noise increase can be suppressed at the time of gain adjustment by performing the gain adjustment such that the gain of an original color signal is adjusted to conform to gain of a complementary color signal that is smaller than the gain of the original color signal.

First Modified Example

Figures 7, 8:
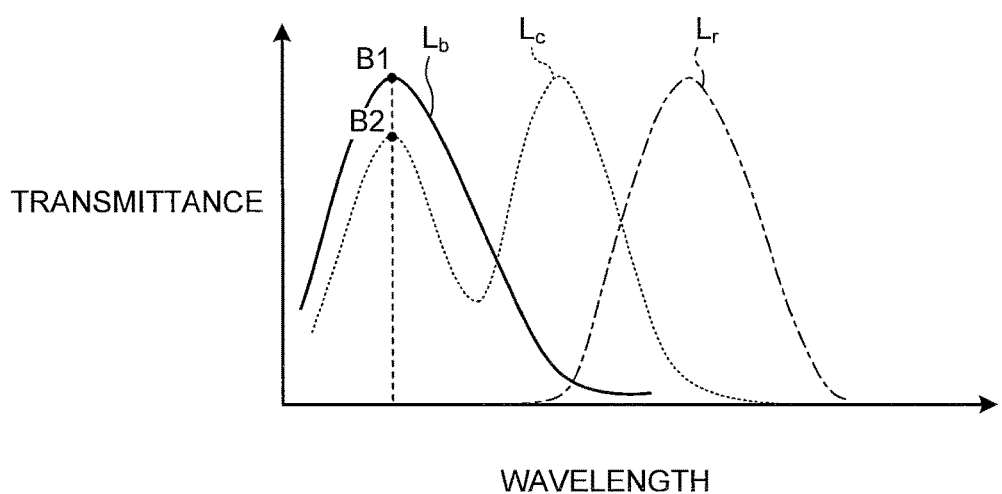
FIG. 7 is a schematic diagram illustrating a structure of a color filter according to a first modified example of the embodiment of the present invention.
FIG. 8 is a diagram illustrating exemplary characteristics of respective filters in the color filter according to the first modified example of the embodiment of the present invention.

FIG. 7 is a schematic diagram illustrating a structure of a color filter according to a first modified example of the embodiment. The color filter according to the present first modified example is formed by two-dimensionally arraying filter units U2 each including four filters arranged in a 2×2 matrix. The filter unit U2 includes one B filter that passes light of the wavelength band $H_B$, two Cy filters that pass light of the wavelength bands $H_B$, $H_G$, and one R filter that passes light of the wavelength band $H_R$.

The Cy filter passes the light of a wavelength band of cyan that is a complementary color of red. In other words, the Cy filter absorbs the light of the wavelength band $H_R$ and passes the light of wavelength band $H_B$, and further passes the light of the wavelength band $H_G$.

In the filter unit U2, the number of the filters for passing the light of the wavelength band $H_G$ (Cy filter) is two, and the number of the filters for passing the light of the wavelength band $H_B$ (B filter and Cy filter) is three.

FIG. 8 is a diagram illustrating exemplary characteristics of the respective filters in the color filter according to the first modified example of the embodiment, and illustrates a relation between a light wavelength and transmittance (sensitivity) of each filter. In FIG. 8, a transmittance curve is normalized such that maximum values of the transmittance of the filters are identical. A curve $L_b$ (solid line) illustrated in FIG. 8 represents a transmittance curve of the B filter, a curve $L_c$ (dotted line) represents a transmittance curve of the Cy filter, and a curve $L_r$ (dot-and-dash line) represents a transmittance curve of the R filter.

In the case of the narrow band imaging method, an electric signal (pixel value) including the B signal and G signal corresponding to the light of the narrow band $T_B$ and the light of the narrow band $T_G$ is output from the Cy pixel. A signal value of the G component out of the pixel value of the Cy pixel can be calculated by using, for example: a pixel value of the adjacent B pixel; a signal value of the B component; a signal value of the G component; a pixel value of the Cy component in the Cy pixel; and a ratio (sensitivity ratio) $\alpha$ ($\alpha=B2/B1$) between transmittance (sensitivity) B1 in the B filter for the light of the wavelength band $H_B$ and transmittance (sensitivity) B2 in the Cy filter for the light of the wavelength band $H_B$. For example, provided that a pixel value obtained from a pixel $P_{11}$ corresponding to the B pixel is $b_{11}$, a pixel value of the Cy component obtained from a pixel $P_{12}$ corresponding to the Cy pixel is $bg_{12}$, a signal value of the B component in the pixel value $bg_{12}$ is $b_{12}$, and a signal value of the G component in the signal value $bg_{12}$ is $g_{12}$, a pixel value $g_{12}$ can be obtained by calculating $g_{12}=bg_{12}-\alpha b_{11}$. Note that the transmittance (sensitivity) B1 and transmittance (sensitivity) B2 are preliminarily obtained by calibration and stored in the storage unit 43 or the like.

Second Modified Example

FIG. 9 is a schematic diagram illustrating a structure of a color filter according to a second modified example of the embodiment The color filter according to the present second modified example is formed by two-dimensionally arraying filter units U3 each including four filters arranged in a 2×2 matrix. The filter unit U3 includes one B filter that passes light of the wavelength band $H_B$, two Cy filters that pass light of the wavelength bands $H_B$, $H_G$, and one Mg filter that passes light of the wavelength bands $H_B$, $H_R$.

In the filter unit U3, the number of the filters for passing the light of the wavelength band $H_G$ (Cy filter) is two, and the number of the filters for passing the light of the wavelength band $H_B$ (B filter, Cy filter, Mg filter) is four.

Third Modified Example

FIG. 10 is a schematic diagram illustrating a structure of a color filter according to a third modified example of the embodiment The color filter according to the present third modified example is formed by two-dimensionally arraying filter units U4 each including four filters arranged in a 2×2 matrix. The filter unit U4 includes one B filter that passes light of the wavelength band $H_B$, two Cy filters that pass light of the wavelength bands $H_B$, $H_G$, and one W filter that passes light of the wavelength bands $H_B$, $H_G$, $H_R$.

The W filter passes light of a white wavelength band. In other words, the W filter has sensitivity for the light of the wavelength bands $H_B$, $H_G$, $H_R$ (white light). Note that an empty (transparent) filter area may also be provided instead of the W filter.

In the filter unit U4, the number of the filters for passing the light of the wavelength band $H_G$ (Cy filter and W filter) is three, and the number of the filters for passing the light of the wavelength band $H_B$ (B filter, Cy filter, W filter) is four.

Fourth Modified Example

FIG. 11 is a schematic diagram illustrating a structure of a color filter according to a fourth modified example of the embodiment. The color filter according to the present fourth modified example is formed by two-dimensionally arraying filter units U5 each including sixteen filters arranged in a 4×4 matrix. The filter unit U5 includes a plurality of the above-described B filters, G filters, and Mg filters respectively, and the respective G filters are arranged diagonally.

In the filter unit U5, the number of the filters for passing the light of the wavelength band $H_G$ (G filter) is eight, and the number of the filters for passing the light of the wavelength band $H_B$ (B filter and Mg filter) is eight.

Fifth Modified Example

FIG. 12 is a schematic diagram illustrating a color filter according to a fifth modified example of the embodiment. The color filter according to the present fifth modified example is formed by two-dimensionally arraying filter units U6 each including sixteen filters arranged in a 4×4 matrix. The filter unit U6 includes a plurality of the above-described B filters, Mg filters, and W filters respectively, and the respective W filters are arranged diagonally.

In the filter unit U6, the number of the filters for passing light of the wavelength band $H_G$ (W filter) is eight, and the number of the filters for passing light of the wavelength band $H_B$ (B filter, Mg filter, W filter) is sixteen.

The color filter 202a according to the above-described embodiment has the filter unit in which the number of filters for passing the light of the wavelength band $H_G$ is to be half or more of the number of filters constituting the filter unit, and further the number of filters for passing the light of the wavelength band $H_B$ is to be equal to or more than the number of filters for passing the light of the wavelength band $H_G$. The color filter can apply any array that satisfies the above-described conditions besides the above-described arrays.

Further, in the above-described embodiment, it has been described that the light receiving surface of the image sensor 202 is provided with the color filter 202a including the plurality of filters each passing the light of the predetermined wavelength band. However, each of the filters may be individually provided in each of the pixels of the image sensor 202.

It has been described that, in the endoscope apparatus 1 according to the above-described embodiment, the illumination light emitted from the illumination unit 31 is switched between the white illumination light and the narrow-band illumination light by inserting and removing the switch filter 31c relative to the white light emitted from the light source 31a. However, either the white illumination light or the narrow-band illumination light may be emitted by switching between two light sources that respectively emit the white illumination light and the narrow-band illumination light. In the case of emitting either the white illumination light or the narrow-band illumination light by switching between the two light sources, it can be applicable to a capsule-shaped endoscope that includes a light source unit, a color filter, and an image sensor and is inserted into a subject.

Further, it has been described that the endoscope apparatus 1 according to the above-described embodiment has the A/D converter 205 provided at the distal end portion 24, but the A/D converter 205 may also be provided at the processor unit 4. Further, a configuration related to the image processing may also be provided at the endoscope 2, a connector to connect the endoscope 2 and the processor unit 4, the operating unit 22, or the like. Furthermore, in the above-described endoscope apparatus 1, it has been described that the endoscope 2 connected to the processor unit 4 is identified by using the identification information and the like stored in the identification information storage unit 261, but an identification means may be provided at a connecting portion (connector) between the processor unit 4 and the endoscope 2. For example, an identification pin (identification means) may be provided on the endoscope 2 side to identify the endoscope 2 connected to the processor unit 4.

According to some embodiments, it is possible to obtain high-resolution images under both of a white light imaging method and a narrow band imaging method.

As described above, the endoscope apparatus according to some embodiments is useful for obtaining high-resolution images under both of the white light imaging method and the narrow band imaging method.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:
1. An endoscope apparatus comprising:
   a light source unit configured to emit white illumination light including red wavelength band light, green wavelength band light, and blue wavelength band light, or to emit narrow-band illumination light including narrow band light included in each of blue and green wavelength bands;

an image sensor having a plurality of pixels arranged in a lattice pattern, each of which is configured to receive light, the image sensor being configured to perform photoelectric conversion on the light received by each of the plurality of pixels to generate an electric signal;

a color filter comprising a filter unit arranged correspondingly to the plurality of pixels, the filter unit including a plurality of filters having a filter for passing the blue wavelength band light, a filter for passing the blue wavelength band light and the green wavelength band light, and a filter for passing at least the red wavelength band light, or the filter unit including a plurality of filters having a filter for passing the blue wavelength band light, a filter for passing the blue wavelength band light and the red wavelength band light, and a filter for passing at least the green wavelength band light, the number of filters for passing the green wavelength band light being half or more of the number of all the filters of the filter unit, and the number of filters for passing the blue wavelength band light being equal to or more than the number of filters for passing the green wavelength band light;

a first gain adjustment unit configured to adjust a gain of the electric signal generated by the image sensor based on the light received by each of the plurality of pixels via the color filter;

a demosaicing processing unit configured to generate image signals of color components respectively that pass through the filter unit based on the electric signal whose gain has been adjusted by the first gain adjustment unit;

a color conversion processing unit configured to separate color components from an image signal having a blue component and at least one of a green component or a red component out of the image signals generated by the demosaicing processing unit to obtain an image signal of the green component or the red component when the light source unit emits the white illumination light, and configured to generate image signals of the blue component, the green component, and the red component, respectively; and a second gain adjustment unit configured to adjust a gain of at least part of the image signals of the blue component, the green component, and the red component generated by the color conversion processing unit.

2. The endoscope apparatus according to claim 1, wherein the filter unit includes a filter for passing the blue wavelength band light, and the green wavelength band light or the red wavelength band light.

3. The endoscope apparatus according to claim 1, wherein the filter unit includes a filter for passing the red wavelength band light, the green wavelength band light, and the blue wavelength band light.

4. The endoscope apparatus according to claim 1, wherein each of the first and second gain adjustment units is configured to set a signal of a color component having a largest gain as a reference, and to adjust a gain of a signal of a color component other than the color component set as the reference.

5. The endoscope apparatus according to claim 1, wherein each of the first and second gain adjustment units is configured to set a signal of a color component having a smallest gain as a reference, and to adjust a gain of a signal of a color component other than the color component set as the reference.

* * * * *